US006271435B1

United States Patent
Serhan (12)

(10) Patent No.: US 6,271,435 B1
(45) Date of Patent: Aug. 7, 2001

(54) LEUKOTRIENE B$_4$ RECEPTOR TRANSGENIC MICE

(75) Inventor: Charles N. Serhan, Wellesley, MA (US)

(73) Assignee: Brigham & Women's Hospital, Inc., Boston, MA (US)

(*) Notice: Subject to any disclaimer, the term of this patent is extended or adjusted under 35 U.S.C. 154(b) by 0 days.

(21) Appl. No.: 09/524,302

(22) Filed: Mar. 14, 2000

Related U.S. Application Data

(60) Provisional application No. 60/125,196, filed on Mar. 18, 1999.

(51) Int. Cl.$^7$ .................... A01K 67/027; A01K 67/00; G01N 33/00; C12P 21/00; C12N 15/00
(52) U.S. Cl. ........................ 800/18; 800/3; 800/4; 800/9; 800/14; 800/18; 800/25; 435/320.1; 435/455; 530/350; 536/23.1
(58) Field of Search ................... 800/3, 4, 9, 14, 800/18, 25; 530/350; 536/23.1

(56) References Cited

PUBLICATIONS

International Search Report, Sep. 19, 2000.
Chiang, N., et al., "Leukotriene B$_4$ Receptor Transgenic Mice Reveal Novel Protective Roles for Lipoxins and Aspirin–Triggered Lipoxins in Reperfusion" *J. of Clin. Invest.*, vol. 104, No. 3, 309–316 (Aug. 1999).
Yokomizo, T. et al., "Human mRNA For Leukotriene B$_4$ Receptor, Complete CDS" EMBL Database Entry HSD0781; Accession No. D89078 (Jun. 15, 1997) XP002146450.
Yokomizo, T., et al., "Leukotriene B$_4$ Receptor Cloning and Intracellular Signaling" *Am. J. of Resp. Crit. Care Med.*, vol. 161, No. 2, 551–555 (Feb. 2000).
Weissmann, G., Smolen, J.E., and Korchak, H.M. 1980. Release of inflammatory mediators from stimulated neutrophils. *N. Engl. J. Med.* 303: 27–34.
Sammuelsson, B. 1983. Leukotrienes: Mediators of immediate hypersensitivity reactions and inflammation. *Science* 220: 568–575.
Owman, C. 1998. The leukotriene B$_4$ receptor functions as a novel type of coreceptor mediating entry of primary HIV–1 isolates into CD4–positive cells. *Proc. Natl. Acad. Sci. USA* 95: 9530–9534.
Marcus, A.J. 1995. Aspirin as prophylaxis against colorectal cancer. *N. Eng. J. Med.* 333:656–658.
Serhan, C.N. 1997. Lipoxins and novel aspirin–triggered 15–epi–lipoxins (ATL): a jungle of cell–cell interactions or a therapeutic opportunity *Prostaglandins* 53: 107–137.
Chiang, N., Takano, T., Clish, C.B., Petasis, N.A. and Serhan C.N. 1998. Aspirin–triggered 15–epi–Lipoxin A$_4$ (ATL) generation by human leukocytes and murine peritonitis exudates: development of a specific 15–epi–LXA$_4$ ELISA. *J. Phar. Exp. Ther.* 287: 779–790.

Takano, T., Clish, C.B., Gronert, K., Petasis, N.A. and Serhan, C.N. 1997. Neutrophil–mediated changes in vascular permeability are inhibited by topical application of aspirin–triggered 15–epi–lipoxin A$_4$ and novel lipoxin B$_4$ stable analogues. *J. Clin. Invest.* 101: 819–826.

Yokomizo, T., Izumi, T., Chang, K., Takuwa, Y. and Shimizu, T. 1997. A G–protein–coupled receptor for leucotriene B$_4$ that mediates chemotaxis. *Nature* 387: 620–624.

Huang, W.–W., Garcia–Zepeda, E.A., Sauty, A., Oettgen, H.C., Rothenberg, M.E. et al. 1998. Molecular and biological characterization of the murine leukotriene B$_4$ receptor expressed on eosinophil. *J. Exp. Med.* 188: 1063–1074.

Toh, H., Ichikawa, A. and Narumiya, S. 1995. Molecular evolution of receptors for eicosanoids. *FEBS Letters* 361: 17–21.

Fiore, S., Romano, M., Reardon, E.M. and Serhan, C.N. 1993. Induction of functional lipoxin A$_4$ receptors in HL–60 cells. *Blood* 81: 3395–3403.

Ng, C.F., Sun, F.F., Taylor, B.M., Wolin, M.S. and Wong, P.Y. 1991. Functional properties of guinea pig eosinophil leukotriene B$_4$ receptors. *J. Immunol.* 147: 3096–3103.

Gronert, K., Colgan, S.P. and Serhan, C.N. 1998. Characterization of human neutrophil and endothelial cell ligand–operated extracellular acidification rate by microphysiometry: impact of reoxygenation. *J. Phar. Exp. Ther.* 285: 252–261.

Goldman, G., Welbourn, R., Klausner, J.M., Kobzik, L., Valeri, C.R. et al. 1992. Mast cells and leukotrienes mediate neutrophil sequestration and lung edema after remote ischemic in rodents. *Surgery* 112: 578–586.

Chen, X.–S., Sheller, J.R., Johnson, E.N. and Funk, C.D. 1994. Role of leukotrienes revealed by targeted disruption of the 5–lipoxygenase gene. *Nature* 372: 179–182.

(List continued on next page.)

*Primary Examiner*—Scott D. Priebe
*Assistant Examiner*—Peter Paras, Jr.
(74) *Attorney, Agent, or Firm*—Nutter, McClennen & Fish LLP; Scott Rothenberger, Esq.

(57) ABSTRACT

The present invention describes a non-human transgenic mouse that produces in its leukocytes, a recombinant human leukotriene B$_4$ receptor (BLTR), having physiological activity of human BLTR. The transgenic mouse has stably integrated into its genome an exogenous gene construct which includes (A) 5' expression regulating sequences, including a BLTR specific promoter, (B) DNA encoding the BLTR and a signal sequence effective in directing overexpression of the BLTR into leukocytes of the transgenic mouse and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mouse.

9 Claims, 6 Drawing Sheets

OTHER PUBLICATIONS

Dziennis, S., Van Etten, R.A., Pahl, H.L., Morris, D.L., Rothstein, T.L. et al. 1995. The CD11b promoter directs high-level expression of reporter genes in macrophage in transgenic mice. *Blood* 85: 319–329.

Gelman, S. 1995. The pathophysiology of aortic cross-clamping and unclasping. *Anesthesiology* 82: 1026–1060.

Capodici, C., Pillinger, M.H., Han, G., Phillips, M.R. and Weissmann, G. 1998. Integrin–dependent homotypic adhesion of neutrophils. Arachidonic acid activates Raf–1/Mek/Erk via a 5–lipoxygenase–dependent pathway. *J. Clin. Invest.* 102: 165–175.

Gronert, K., Gewirtz, A., Madara, J.L. and Serhan, C.N. 1998. Identification of a human enterocyte lipoxin $A_4$ receptor that is regulated by interleukin (IL)–13 and interferon γ and inhibits tumor necrosis factor α–induced and IL–8 release. *J. Exp. Med.* 187: 1285–1294.

Ebert et al, 1988, Mol. Endocrinol., 2: 277–283.*
Hammer et al, 1986, J. Anim. Sci., 63: 269–278.*
Houdebine et al, 1994, J. Biotechnol., 34: 269–287.*
Kappel et al, 1992, Cur. Opin. Biotechnol., 3: 548–553.*
Mullins et al, 1996, J. Clin. Invest., 98: S37–40.*
Strojek et al, 1988, Genetic Engineering: Principles and Methods, 10:221–246, Plenum Press.*
Wall et al, 1996, Theriogenology, 45: 57–68.*

* cited by examiner ized.

LEUKOTRIENE B₄ RECEPTOR TRANSGENIC MICE

CROSS-REFERENCE TO RELATED APPLICATIONS

This application claims priority to U.S. provisional patent application No. 60/125,196 filed Mar. 18, 1999, the contents of which are incorporated herein by reference.

The work leading to this invention was supported by National Institutes of Health grant numbers GM38765 and DK50305. The U.S. Government therefore may have certain rights in the invention.

BACKGROUND OF THE INVENTION

PMN recruitment and sequestration to sites of inflammation and second organ injury is initiated by pro-inflammatory mediators, among which $LTB_4$ is considered to be very important (Weissmann, G., Smolen, J. E., and Korchak, H. M. 1980. Release of inflammatory mediators from stimulated neutrophils. *N. Engl. J. Med.* 303: 27–34; Sammuelsson, B. 1983. Leukotrienes: Mediators of inflammation and immediate hypersensitivity. *Science* 220: 568–575). Recently, the $LTB_4$ receptor (BLTR) was also shown to serve as a coreceptor for HIV-1 entry, which further emphasizes the crucial role of this system in host defense (Owman, C. 1998. The leukotriene $B_4$ receptor functions as a novel type of coreceptor mediating entry of primary HIV-1 isolates into CD4-positive cells. *Proc. Natl. Acad. Sci. USA* 95: 9530–9534). Aspirin is widely used for its anti-inflammatory and analgesic properties with several newly identified therapeutic actions including prevention of cardiovascular diseases and decreasing incidence of lung, colon and breast cancers, which increases the importance of obtaining complete knowledge of aspirin's mechanism of action (Marcus, A. J. 1995. Aspirin as prophylaxis against colorectal cancer. *N. Eng. J. Med.* 333: 656–658). When aspirin is given, in addition to inhibiting prostanoid biosynthesis, it also triggers the endogenous transcellular production of 15 epimeric or 15R $LXA_4$, termed aspirin-triggered $LXA_4$ (ATL), which appears to mediate in part some of aspirin's therapeutic impact and is generated in vivo (Serhan, C. N. 1997. Lipoxins and novel aspirin-triggered 15-epi-lipoxins (ATL). *Prostaglandins* 53: 107–137; Chiang, N., Takano, T., Clish, C. B., Petasis, N. A. and Serhan C. N. 1998. Aspirin-triggered 15-epi-Lipoxin $A_4$ (ATL) generation by human leukocytes and murine peritonitis exudates: development of a specific 15-epi-$LXA_4$ ELISA. *J. Phar. Exp. Ther.* 287: 779–790). $LXA_4$ controls leukocyte responses via its own specific G protein coupled receptor, denoted ALXR, which also engages 15-epi-$LXA_4$ (Serhan, C. N. 1997. Lipoxins and novel aspirin-triggered 15-epi-lipoxins (ATL). *Prostaglandins* 53: 107–137; Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$, and novel lipoxin $B_4$ stable analogues. *J. Clin. Invest.* 101: 819–826). Like other local mediators, LXs are rapidly generated, evoke responses and are inactivated by further metabolism (Serhan, C. N. 1997. Lipoxins and novel aspirin-triggered 15-epilipoxins (ATL). *Prostaglandins* 53: 10714 137). Methods to monitor, study and screen potential pharmaceuticals, e.g., antiinflammatories, which interact with the identified receptors, therefore, are of interest.

SUMMARY OF THE INVENTION

In one aspect the present invention pertains to a non-human transgenic mammal that produces in its leukocytes a recombinant human leukotriene $B_4$ receptor (BLTR) having physiological activity of human BLTR. The transgenic mammal has stably integrated into its genome an exogenous gene construct which includes (A) 5' expression regulating sequences, including a BLTR specific promoter, (B) DNA encoding the BLTR and a signal sequence effective in directing overexpression of the BLTR into leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal.

In another aspect, the invention pertains to a process for producing recombinant human BLTR having physiological activity of human BLTR. The method includes providing a non-human transgenic mammal having integrated into its genome an exogenous gene construct that includes (A) 5' expression regulating sequences, including a BLTR specific promoter, (B) DNA encoding the BLTR and a signal sequence effective in directing overexpression of the BLTR in leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal. The BLTR is overexpressed and secreted in the leukocytes of the transgenic mammal.

In yet another aspect, the present invention pertains to a process for producing a non-human transgenic mammal that produces in its leukocytes a recombinant human leukotriene $B_4$ receptor (BLTR) having physiological activity of human BLTR. The method includes (a) providing an exogenous gene construct that includes (A) 5' expression regulating sequences, including a BLTR specific promoter, (B) DNA encoding the BLTR and a signal sequence effective in directing overexpression of the BLTR in leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal. The construct of step (a) is introduced into a non-human mammalian embryo, wherein the construct is stably integrated into the genome of the mammalian embryo. The embryo is allowed to develop into a non-human transgenic mammal and it is determined whether the non-human transgenic mammal of (c) overexpresses BLTR.

In still another aspect, the present invention pertains to a method for screening compounds that inhibit overexpression of polymorphonuclear leukocyte production in a non-human transgenic mammal that produces in its leukocytes a recombinant human leukotriene $B_4$ receptor (BLTR) having physiological activity of human BLTR. The method includes (a) providing a non-human transgenic mammal having integrated into its genome an exogenous gene construct which includes (A) 5' expression regulating sequences, including a BLTR specific promoter, (B) DNA encoding the BLTR and a signal sequence effective in directing overexpression of the BLTR into leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal. The BLTR is allowed to be overexpressed and secreted in the leukocytes of the transgenic mammal. The transgenic mammal can be subjected to physiological stressing, thereby causing increased neutrophil recruitment to the leukocytes via the overexpressed BLTR. A therapeutically effective amount of a compound is administered to the mammal to interact with the neutrophil recruitment in response to the stress. It is then determined empirically, whether the compound, e.g., an lipoxin derivative, reduces neutrophil activation in the leukocytes of the transgenic mammal which have overexpress BLTR therein. Alternatively, step (d) is performed prior to step (c), thereby preventing or inhibiting neutrophil activation.

In one preferred embodiment the transgenic mammal produces human BLTR. In another preferred embodiment, the human BLTR has the amino acid sequence of human BLTR. In still another preferred embodiment, the mammal is selected from the group consisting of rat, rabbit, pig, sheep, goat or cow, and most preferably a mouse. It is preferred that the mammal is a female, e.g., a female mouse.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
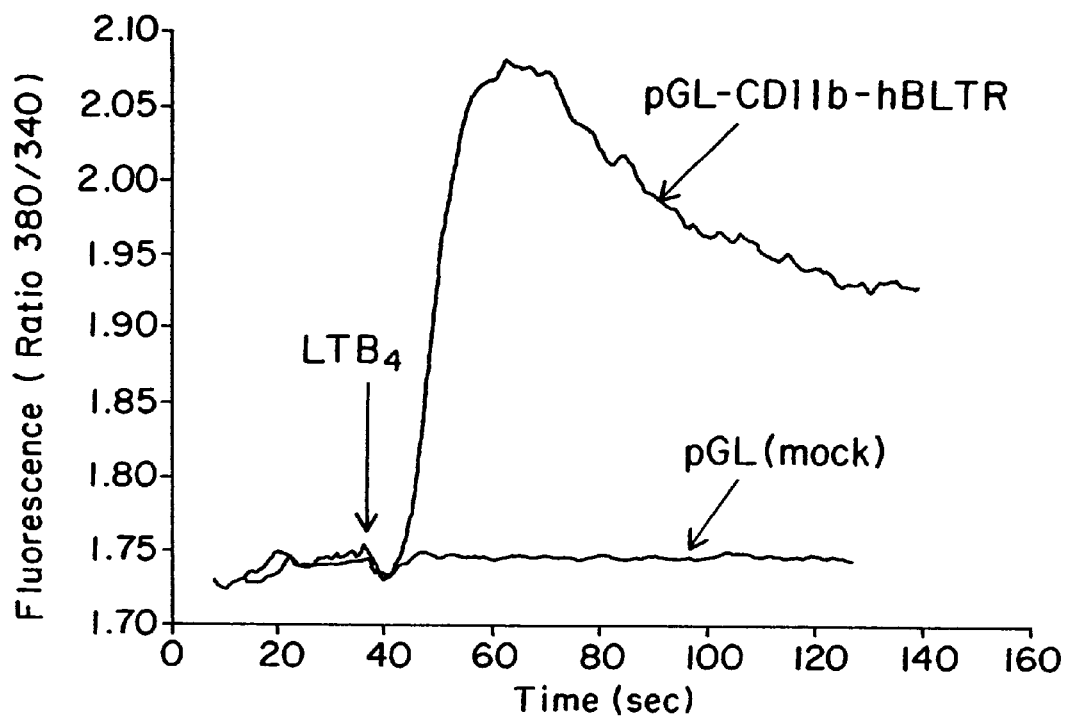
FIG. 1 (A–E)demonstrates that topical application of $LXA_4$ inhibits PMN infiltration in hBLTR transgenic mice without interfering with $LTB_4$-BLTR recognition. (A) pGL-CD11b-hBLTR and mock (pGL) plasmids were transiently transfected into HEK293 cells, and intracellular $Ca^{2+}$ was mobilized by addition of $LTB_4$ (100 nM). (B) $LTB_4$ (1 µg) was applied topically to the right ears of wt mice (hatched bar) and transgenic mice (filled bar). Left ears received vehicle alone (acetone). Ear skin biopsy samples were taken for MPO analysis and values represent fold increase above vehicle control (*p<0.01, n=7 for wt and n=10 for TG-hBLTR). BLTR expression in wt and hBLTR transgenic mice was analyzed by RT-PCR using hBLTR -III and hBLTR -VII primers that gave the expected bands at ~0.5 kb as indicated by an arrow (inset). (C) The $LXA_4$ stable analog (10 µg) 16-phenoxy-$LXA_4$ (inset: $LXA_4$ analog template $R_2$=phenoxy) was applied topically to right ears of wt and hBLTR transgenic mice (gray). Left ears received vehicle alone (black). $LTB_4$ (1 µg) was then applied to both ears of each mouse 5 min later. Skin biopsies were obtained as above. Values represent total PMN infiltration into ear skin (representative data from n=3). (D) Displacement of specific [$^3$H]-$LTB_4$ binding by $LTB_4$ (square, structure shown), $LXA_4$ (diamond) or $LXB_4$ (circle) was determined in HEK293 cells stably transfected with BLTR. (E) Extracellular acidification rate (EAR)s in response to $LXA_4$ and $LTB_4$ were analyzed by Cytosensor microphysiometry in HEK293 cells with BLTR and ALXR (stable transfectants). Cells were exposed to $LXA_4$ (1 µM, open circle) or media alone (filled circle) 20 min prior to exposure to $LTB_4$ (1 µM). Values are expressed as EAR (µV/s) normalized to baseline (100%), and ligand additions are indicated by arrows.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Abbreviations: ALXR, lipoxin $A_4$ receptor; ATL, aspirin-triggered 15-epi-$LXA_4$ (analog of ATL: 15-epi-16-para-fluoro-phenoxy-$LXA_4$ (15(R)-16-para-fluoro-phenoxy-17, 18,19,20-tetranol-$LXA_4$ methyl ester)); BLTR, leukotriene $B_4$ receptor; 5S-HETE, 5S-hydroxyl-8, 11, 14-cis-6-trans-eicosatetraenoic acid; LC/MS/MS, liquid chromatography tandem mass-spectrometry-mass spectrometry; LO, lipoxygenase; LT, leukotriene; LX, lipoxin; $LXA_4$, 5(S), 6(R), 15(S)-trihydroxy-7, 9, 13-trans-11-cis eicosatetraenoic acid; MPO, myeloperoxidase; and RT-PCR, reverse transcription-polymerase chain reaction. Suitable methods of preparation of lipoxin compounds can be found, for example, in U.S. Pat. Nos. 5,411,951, 5,648,512, 5,650,435 and 5,750,354, incorporated herein by reference.

Neutrophil (PMN) activation is pivotal in acute inflammation and injury from reperfusion. To elucidate components controlling neutrophils in vivo, novel transgenic mice were prepared with the human leukotriene (LT) $B_4$ receptor (BLTR) for functional characterization. Transgenic animals according to the invention comprise a nucleic acid sequence comprising a gene encoding BLTR or variant thereof, and are capable of overexpressing the gene. The nucleic acid may be of natural or artificial origin. It may be genomic DNA (gDNA), complementary DNA (cDNA), hybrid sequences or synthetic or semisynthetic sequences. It may be of human, animal, plant, bacterial or viral origin and the like. It may be obtained by any technique known to persons skilled in the art, for example, by chemical synthesis, or alternatively by mixed methods including chemical or enzymatic modification of sequences. It is preferably cDNA or gDNA. The complete DNA and amino acid sequences for human BLTR is disclosed in Yokomizo et al. (1997) *Nature* 387: 620–624, the entire contents of which are incorporated herein by reference, and can also be found at GenBank Accession No. NM 000752.

Overexpression of BLTR in leukocytes dramatically increased PMN trafficking to skin microabscesses and lungs following ischemia-reperfusion, whereas 5-lipoxygenase (LO) deficient mice gave diminished PMN accumulation in reperfused lungs. Hence, both BLTR expression and LT biosynthesis are critical for PMN infiltration in reperfusion-initiated second organ injury. Also, in BLTR transgenic mice, 5-LO expression and product formation were selectively increased in exudates, demonstrating that receptor overexpression amplifies pro-inflammatory circuits. Endogenous lipoxin (LX) $A_4$ was produced in ischemic lungs and elevated by reperfusion. Since $LXA_4$ and aspirin-triggered 15-epimeric $LXA_4$ (ATL) generated with aspirin treatment selectively regulate leukocyte responses, they are tested in BLTR transgenic mice. Despite excessive PMN recruitment in BLTR transgenic mice, intravenous injection of ATL sharply diminished reperfusion-initiated PMN trafficking to remote organs, and topical $LXA_4$ was protective in acute dermal inflammation. These results demonstrate a direct role for BLTR with positive feedback involving BLTR and 5-LO signaling in controlling PMN. Moreover, $LXA_4$ and ATL counter BLTR-amplified network(s) revealing a novel protective role for LX and ATL in stress responses that has applications in perioperative medicine.

Recent cloning of BLTR in human and mouse permitted the elucidation of this signaling pathway at the receptor and gene level (Yokomizo, T., Izumi, T., Chang, K., Takuwa, Y. and Shimizu, T. 1997. A G-protein-coupled receptor for leukotriene $B_4$ that mediates chemotaxis. *Nature* 387: 620–624; Huang, W—W., Garcia-Zepeda, E. A., Sauty, A., Oettgen, H. C., Rothenberg, M. E. et al. 1998. Molecular and biological characterization of the murine leukotriene $B_4$ receptor expressed on eosinophils. *J. Exp. Med.* 188: 1063–1074). Each of these BLTRs shows homology with ALXR and the chemokine and chemotactic peptide family of receptors (~30%) exemplified by fMLP, C5a and IL-8 receptors, but not to the prostanoid receptors, providing further evidence that the origin of receptors for LX and LT is distinct from that for prostanoids (Toh, H., Ichikawa, A. and Narumiya, S. 1995. Molecular evolution of receptors for eicosanoids. *FEBS Letters* 361:17–21). Along these lines, transgenic mice were developed with human BLTR (hBLTR). Utilizing these novel BLTR transgenic mice in conjunction with available 5-LO deficient mice, it was demonstrated that $LXA_4$ and ATL regulate PMN-initiated second organ injury in reperfusion and uncover a novel positive circuit in 5-LO signaling (Funk C. D. 1999. in "Molecular and Cellular Basis of Inflammation" (eds. C. N. Serhan and P. A. Ward) Lipidmediator-deficient mice in models of inflammation, pp. 109–125. Humana Press, Totowa, N.J.).

In one aspect the present invention pertains to a non-human transgenic mammal that produces in its leukocytes a recombinant human leukotriene $B_4$ receptor (BLTR) having physiological activity of human BLTR. The transgenic mammal has stably integrated into its genome an exogenous gene construct which includes (A) 5' expression regulating sequences, including a BLTR specific promoter, (B) DNA encoding the BLTR and a signal sequence effective in directing overexpression of the BLTR into leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal.

In another aspect, the invention pertains to a process for producing recombinant human BLTR having physiological activity of human BLTR. The method includes providing a non-human transgenic mammal having integrated into its genome an exogenous gene construct that includes (A) 5' expression regulating sequences, including a BLTR specific promoter, (B) DNA encoding the BLTR and a signal sequence effective in directing overexpression of the BLTR in leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal. The BLTR is overexpressed and secreted in the leukocytes of the transgenic mammal.

In yet another aspect, the present invention pertains to a process for producing a non-human transgenic mammal that produces in its leukocytes a recombinant human leukotriene $B_4$ receptor (BLTR) having physiological activity of human BLTR. The method includes (a) providing an exogenous gene construct that includes (A) 5' expression regulating sequences, including a BLTR specific promoter, (B) DNA encoding the BLTR and a signal sequence effective in directing overexpression of the BLTR in leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal. The construct of step (a) is introduced into a non-human mammalian embryo, wherein the construct is stably integrated into the genome of the mammalian embryo. The embryo is allowed to develop into a non-human transgenic mammal and it is determined whether the non-human transgenic mammal of (c) overexpresses BLTR.

In still another aspect, the present invention pertains to a method for screening compounds that inhibit overexpression of polymorphonuclear leukocyte production in a non-human transgenic mammal that produces in its leukocytes a recombinant human leukotriene $B_4$ receptor (BLTR) having physiological activity of human BLTR. The method includes (a) providing a non-human transgenic mammal having integrated into its genome an exogenous gene construct which includes (A) 5' expression regulating sequences, including a BLTR specific promoter, (B) DNA encoding the BLTR and a signal sequence effective in directing overexpression of the BLTR into leukocytes of the transgenic mammal and (C) 3' regulatory sequences that result in the overexpression of the DNA in the leukocytes. In one embodiment, (A), (B), and (C) are operably linked in the gene construct to obtain production of the BLTR in the leukocytes and overexpression thereof in the transgenic mammal. The BLTR is allowed to be overexpressed and secreted in the leukocytes of the transgenic mammal. The transgenic mammal can be subjected to physiologically stressing, thereby causing increased neutrophil recruitment to the leukocytes via the overexpress BLTR. A therapeutically effective amount of a compound is administered to the mammal to interact with the neutrophil recruitment in response to the stress. It is then determined empirically, whether the compound, e.g., an lipoxin derivative, reduces neutrophil activation in the leukocytes of the transgenic mammal which have overexpress BLTR therein. Alternatively, step (d) is performed prior to step (c), thereby preventing or inhibiting neutrophil activation.

In one preferred embodiment the transgenic mammal produces human BLTR. In another preferred embodiment, the human BLTR has the amino acid sequence of human BLTR. In still another preferred embodiment, the mammal is selected from the group consisting of rat, rabbit, pig, sheep, goat or cow, and most preferably a mouse. It is preferred that the mammal is a female, e.g., a female mouse.

Materials and Methods

Cloning and functional expression of hBLTR. Total RNA was isolated from retinoic acid differentiated HL-60 cells using TriZol reagent (GIBCO BRL, Grand Island, N.Y.) and reverse-transcribed for 30 min at 50° C. followed by 40 cycles of polymerase chain reactions (PCR) using Vent DNA polymerase (New England BioLabs, Beverly, Mass.) (98° C. for 1 min, 60° C. for 1 min and 72° C. for 2 min) with specific primers for HBLTR (BLTR-N: 5'-GCCGGATCC-ATGAACACTACATCTTCTGCA-3' and BLTR-C: 5'-GC-CCTCGAGCTAGTTCAGTTCGTTTAACTT-3') (Fiore, S., Romano, M., Reardon, E. M. and Serhan, C. N. 1993. Induction of functional lipoxin $A_4$ receptors in HL-60 cells. Blood 81: 3395–3403). hBLTR cDNA was inserted into pGL vector (Promega) at HindIII-PpuMI site downstream of CD11b promoter. HEK293 cells were transfected with this pGL-CD11b-hBLTR construct using SuperFect reagent (Qiagen, Chatsworth, Calif.). Ligand binding and intracellular $Ca^{2+}$ release were carried out as in refs. (Yokomizo, T., Izumi, T., Chang, K., Takuwa, Y. and Shimizu, T. 1997. A G-protein-coupled receptor for leukotriene $B_4$ that mediates chemotaxis. Nature 387: 620–624) and (Ng, C. F., Sun, F. F., Taylor, B. M., Wolin, M. S. and Wong, P. Y. 1991. Functional properties of guinea pig eosinophil leukotriene $B_4$ receptors. J. Immunol. 147: 3096–3103), respectively. For stable transfection, hBLTR cDNA was inserted into pcDNA3 vector (Invitrogen, Carlsbad, Calif.) carrying a neomycin resistant gene. hALXR cDNA was inserted into pcDNA6 (Invitrogen, Carlsbad, Calif.) carrying a different selection marker (blasticidin resistant gene). HEK293 cells were transfected with both constructs and selected with both neomycin and blasticidin. Cytosensor microphysiometry analysis of extracellular acidification rate (EAR) was carried out as in (Gronert, K., Colgan, S. P. and Serhan C. N. 1998. Characterization of human neutrophil and endothelial cell ligand-operated extracellular acidification rate by microphysiometry: impact of reoxygenation. J. Phar. Exp. Ther. 285: 252–261).

Preparation and identification of hBLTR transgenic mice. hBLTR transgene was obtained by digestion of the plasmid (pGL-CD11b-hBLTR) with NotI and BamHI and purified by Elutip (Schleicher & Schuell, Keene, N. H.). Purified transgene was injected into mouse (FVB's strain) embryos by microinjection and then transplanted into the foster mothers. The transgenic founder mice that had integrated the transgene were bred with mice of the same strain. Positive litters from the transgenic founder were identified by PCR using the genomic DNA isolated from mouse whole blood. Briefly, 15 µl of blood was collected from each mouse and resuspended in 250 µl of 10 mM Tris-HCl (pH 7.8) containing 1 mM EDTA and 0.5% NP-40. Cellular materials were obtained by centrifugation at 11,000 rpm for 5 min and resuspended in 40 µl of 0.1% TritonX-100 and 10 µl of 0.4 N NaOH to partially digest cell membrane and denature proteins. They were then heated at 95° C. for 5 min, cooled on ice, neutralized with 10 µl of 1M Tris (pH 7.5), and each sample (1 µl) was used for 25 µl PCR. Hot-start PCR (98° C. for 5 min before adding the Vent polymerase) was performed with 40 cycles of amplification (98° C. for 1 min, 60° C. for 1 min and 72° C. for 2 min) with primers BLTR-N and BLTR-C. For verifying hBLTR and 5-LO expression, peritoneal leukocytes from mice with casein-induced peritonitis (2% casein, 4 hr) were collected as in (Chiang, N., Takano, T., Clish, C. B., Petasis, N. A. and Serhan C. N. 1998. Aspirin-triggered 15-epi-Lipoxin $A_4$ (ATL) generation by human leukocytes and murine peritonitis exudates: development of a specific 15-epi-$LXA_4$ ELISA. J. Phar. Exp. Ther. 287: 779–790) and total RNA was isolated. Reverse transcription (RT)-PCR were performed using essentially the same conditions described above using primers BLTR-III: 5'-TACGCCAGCGTCCTGCTT-3' and BLTR-VII: 5'-GCTGCTCAGGAAGGCGAG-3', which amplify both human and mouse BLTR. For amplifying 5-LO, mouse specific sense (5'-ATCAGGACGTTCACG GCCAGG-3') and antisense (5'-CCAGGAACAGCTCGTTTTCCTG-3') primers were used.

Ear skin inflammation model. hBLTR transgenic and wt mice were anesthetized and 16-phenoxyl-$LXA_4$ (15(S)-16-phenoxy-17, 18, 19, 20-tetranol-$LXA_4$ methyl ester, prepared by total synthesis as in ref. 7 by Prof. N. A. Petasis and colleagues, Dept. of Chemistry, Univ. of Southern Calif.) (10 µg) in 10 µl of acetone was applied to the inner side of right ears. Acetone alone was applied to the left ear as a vehicle control. Five min later, $LTB_4$ (5S, 12R-dihydroxy-6, 8, 10, 14-eicosatetraenoic acid; 1 µg) in 10 µl acetone was applied to both ears. Ear skin punch biopsies were collected for leukocyte MPO activity (Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$ and novel lipoxin $B_4$ stable analogues. J. Clin. Invest. 101: 819–826).

Hind limb ischemia-reperfusion induced second organ injury. Mice were anesthetized and ATL analog 15-epi-16-para-fluoro-phenoxy-$LXA_4$ (15(R)-16-para-fluoro-phenoxy17, 18, 19, 20-tetranol-$LXA_4$ methyl ester), prepared as in (Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$ and novel lipoxin $B_4$ stable analogues. J. Clin. Invest. 101: 819–826) or vehicle was administered intravenously to the transgenic mice. Approximately five minutes later, a tourniquet was placed proximally around each hind limb and secured with a metal clamp (Goldman, G., Welbourn, R., Klausner, J. M., Kobzik, L., Valeri, C. R. et al. 1992. Mast cells and leukotrienes mediate neutrophil sequestration and lung edema after remote ischemia in rodents. Surgery 112: 578–586). Vascular occlusion was verified by engorgement and discoloration of the feet. After 3 hours of ischemia, the tourniquets were removed and followed by 3 hours of reperfusion. The 5-LO(+/+) and (−/−) mice (from Jackson Laboratory, Bar Harbor, Me.) as well as hBLTR transgenic mice were then euthanized with an overdose of pentobarbital by intraperitoneal injection in accordance with Harvard Medical Area Standing Committee on Animals (protocol no. 02570-R98) (Chen, X. -S, Sheller, J. R., Johnson, E. N. and Funk, C. D. 1994. Role of leukotrienes revealed by targeted disruption of the 5-lipoxygenase gene. Nature 372:179–182). The left lungs were harvested, homogenized in 1.5 ml of potassium phosphate buffer (pH 7.4) and then centrifuged at 14,000 rpm (5 min). The precipitates were further extracted for leukocyte MPO analysis and the supernatants were stored (−80° C.) for eicosanoid analysis (Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$ and novel lipoxin $B_4$ stable analogues. *J. Clin. Invest.* 101: 819–826).

LC/MS/MS analysis. Murine peritoneal exudates were obtained from casein-induced peritonitis and incubated with A23187 (5 µM) at 37° C. for 30 min. The samples were prepared by solid-phase extraction (SPE) (Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$ and novel lipoxin $B_4$ stable analogues. *J. Clin. Invest.* 101: 819–826) with 10 ng of $d_4$-$LTB_4$ (6, 7, 14, 15-deuterium [$d_4$]-$LTB_4$) added to each as internal standard to calculate recovery. Liquid chromatography-tandem mass spectrometry (LC/MS/MS) was performed with an LCQ (Finnigan Corp., San Jose, Calif.) ion trap mass spectrometer system equipped with an electrospray ionization probe. Samples were suspended in mobile phase and injected into the HPLC component (Thermo Separation Products, San Jose, Calif.), which consisted of a quaternary gradient pump, a LUNA C18-2 (150×2 mm, 5µm) column (Phenomenex, Torrance, Calif.), and a scanning UV/VIS absorbance detector. The column was eluted at 0.2 ml/min isocratically for 20 min with methanol/water/acetic acid (65/35/0.01, v/v/v) followed by a 20 min linear gradient to 99.99/0.01 methanol/acetic acid (v/v). Mass spectra were recorded in the negative ion mode with the spray voltage set to 5 kV, the heated capillary to 250° C., and a maximum ion injection time of 350 ms. Selected ion monitoring (SIM) mass spectra were measured between m/z 315–360 throughout the elution with product ion spectra (MS/MS) recorded for molecular anions ([M—H]−).

Statistical analysis. Results were expressed as the mean ± SEM, and Student's t-test was performed with P values <0.05 taken as statistically significant.

Results and Discussion

Figure 1B:
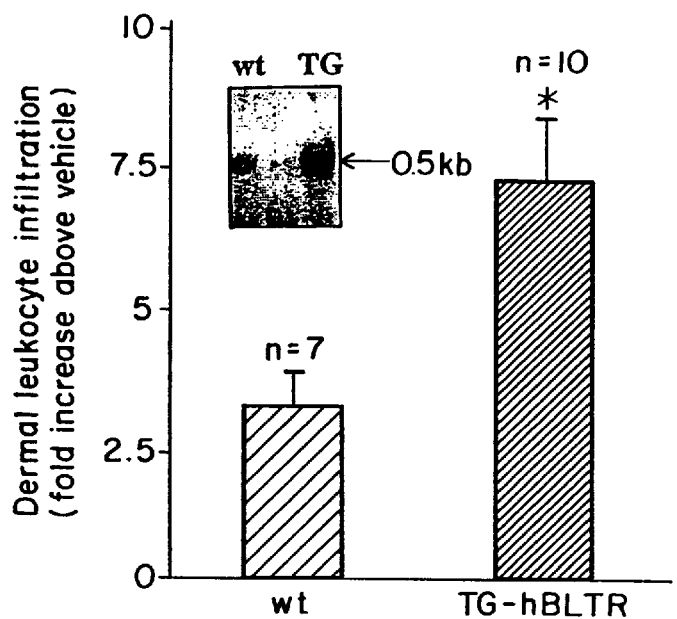

Transgenic mice were prepared for these experiments with human BLTR cloned from retinoid acid differentiated HL-60 cells displaying $LTB_4$ binding and signaling as in (Funk C. D. 1999. In "molecular and Cellular Basis of Inflammation" (eds. C. N. Serhan and P. A. Ward) Lipid-mediator-deficient mice in models of inflammation, pp. 109–125. *Humana Press*, Totowa, N.J.) using reported sequences in (Yokomizo, T., Izumi, T., Chang, K., Takuwa, Y. and Shimizu, T. 1997. A G-protein-coupled receptor for leukotriene $B_4$ that mediates chemotaxis. *Nature* 387: 620–624). This BLTR transgene was placed in control of a CD11b promoter (FIG. 1A) that directs high-level heterologous gene expression in leukocytes as in (Dziennis, S., Van Etten, R. A., Pahl, H. L., Morris, D. L., Rothstein, T. L. et al. 1995. The CD11b promoter directs high-level expression of reporter genes in macrophages in transgenic mice. *Blood* 85: 319–329). To verify the clone, human embryonic kidney cells (HEK293) were transfected with hBLTR cDNA (pGL-CD11b-hBLTR). These cells displayed both specific [$^3$H]-$LTB_4$ binding and ligand stimulated mobilization of intracellular $Ca^{2+}$ (FIG. 1A), qualifying its use for preparing hBLTR transgenic mice. Peritoneal leukocyte exudates (from casein-induced peritonitis) from positive hBLTR transgenic mice were collected and displayed a ~7 fold increase in BLTR message levels compared to wild type (wt) that were age and strain matched (FIG. 1B, inset), indicating that the hBLTR transgene was indeed expressed and total BLTR expression was dramatically increased. Of interest, these hBLTR transgenic mice appeared healthy and without apparent gross pathologic findings in the absence of a specific challenge (vide infra).

$LTB_4$ applied topically to mouse ear skin induces PMN influx and microabscess in an acute dermal inflammatory response (Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$ and novel lipoxin $B_4$ stable analogues. *J. Clin. Invest.* 101:819–826). The transgenic mice of the invention gave a pronounced increase (7.4±0.9 fold) in PMN infiltration into skin (FIG. 1B), whereas the wt response was increased 3.2±0.5 fold compared to vehicle control. In sharp contrast, PMN infiltration into ear skin with either the native precursor of $LTB_4$, namely arachidonic acid (10 µg) or the protein kinase C direct agonist phorbol 12-myristate 13-acetate (100 ng), was not augmented in hBLTR transgenic mice. Both agents were added at levels that did not destroy tissue architecture of the ear skin. These findings indicate that hBLTR was functionally expressed and directly correlated with profound amplification of $LTB_4$-initiated PMN microabscess formation in skin.

Figure 1C:
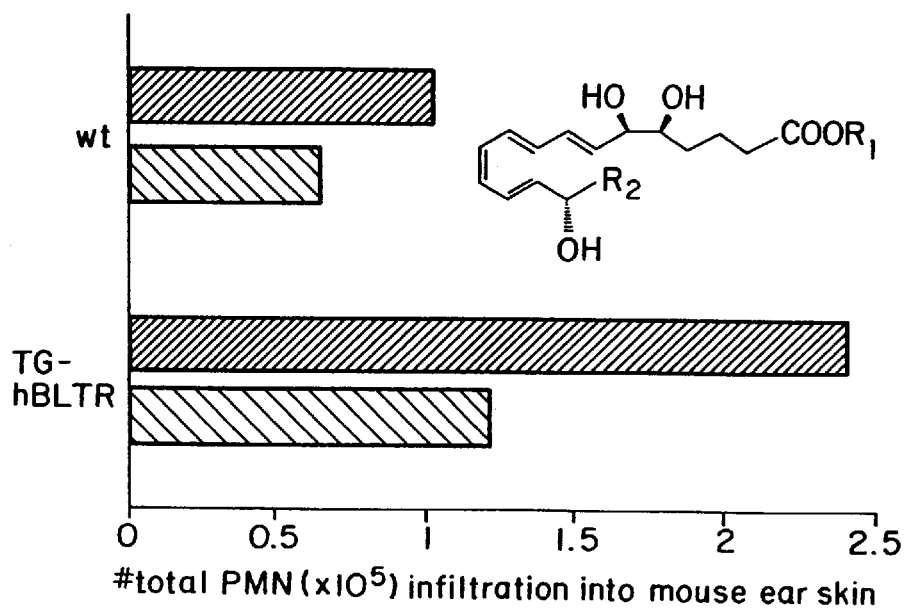
Figure 1D:
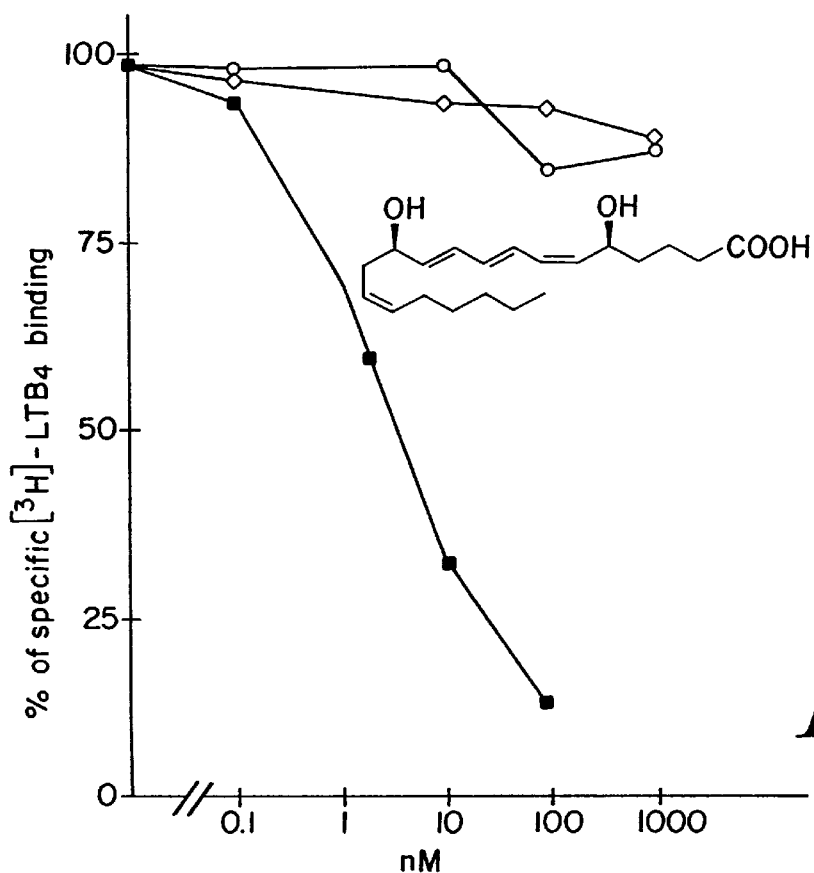
Figure 1E:
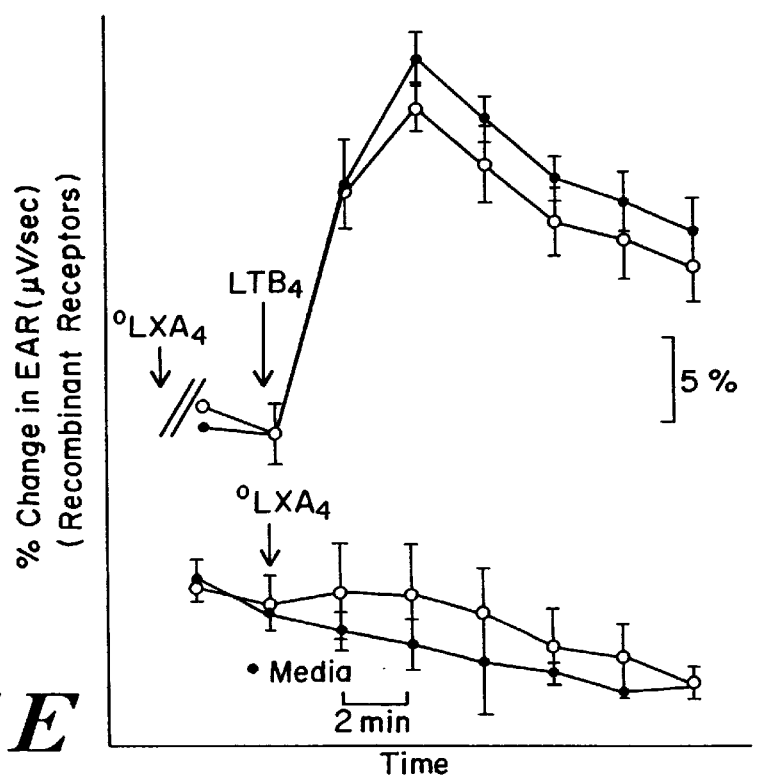

To determine whether $LXA_4$ regulates this amplified $LTB_4$-BLTR signaling pathway and if these BLTR transgenic mice respond to $LXA_4$ as wt mice, a stable LX analog that resists rapid inactivation and mimics $LXA_4$ actions (see FIG. 1C inset for $LXA_4$ analog template structure) was examined for its ability to modulate PMN trafficking (Serhan, C. N. 1997. Lipoxins and novel aspirin-triggered 15-epi-lipoxins (ATL) *Prostaglandins* 53: 107–137; Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin A4 and novel lipoxin B4 stable analogues. *J. Clin. Invest.* 101: 819–826). In spite of excessive PMN infiltration in hBLTR transgenic mice, topical application of the $LXA_4$ stable analog was clearly able to block PMN infiltration (FIG. 1C, representative data from n=3). The percent inhibition in hBLTR transgenic versus wt mice (~45% vs. ~37% inhibition) did not prove to be significantly different. Moreover, in magnitude, the $LXA_4$ stable analog inhibited infiltration of 3 times as many PMN in hBLTR transgenic than in wt mice (FIG. 1C), evident when leukocyte myeloperoxidase (MPO) activities from these punch biopsies were calibrated and converted to total number of PMN. No apparent increases in ALXR message levels were observed. Hence, $LXA_4$ and ALXR constitute a potent system for BLTR regulation in vivo. Specific binding and signaling in HEK293 cells expressing BLTR or BLTR together with ALXR as stable transfectants was examined. $LXA_4$ did not compete with [$^3$H]-$LTB_4$ binding (FIG.1D), nor did $LXA_4$ or its analogs affect $LTB_4$-evoked extracellular acidification rate (FIG .1E) (Gronert, K., Colgan, S. P. and Serhan C. N. 1998.Characterization of human neutrophil and endothelial cell ligand-operated extracellular acidification rate by microphysiometry: impace of reoxygenation. *J. Phar. Exp. Ther.* 285: 252–261). Therefore, ALXR activation inhibits signal transduction components that are post $LTB_4$-BLTR recognition.

Figure 2A:
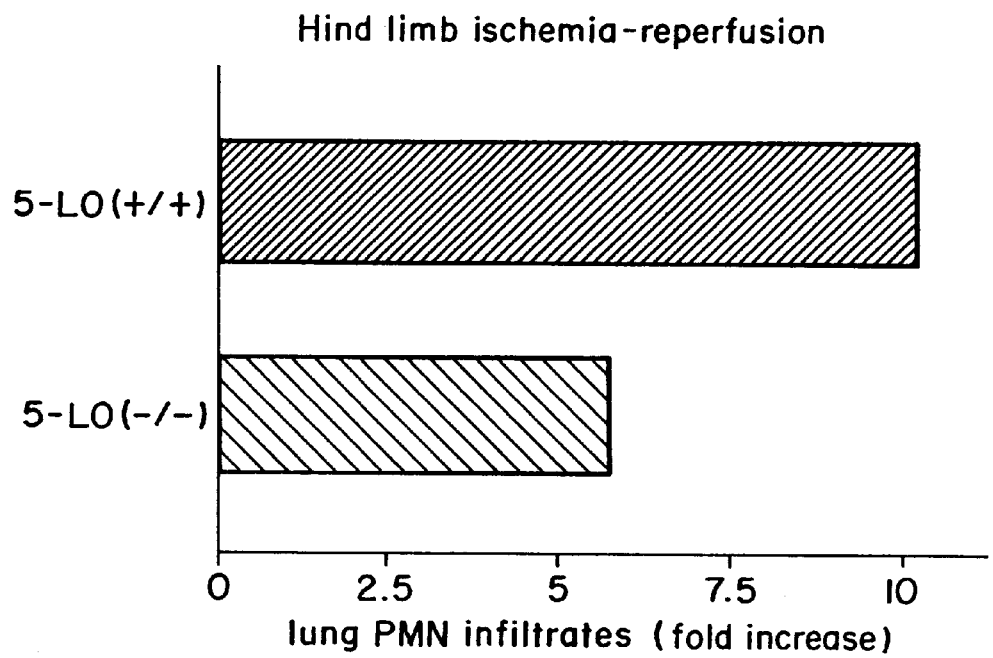
FIG. 2 (A–D) depicts 5-LO pathway and BLTR are major determinants for PMN infiltration into lungs after hind limb ischemia-reperfusion: Inhibition by aspirin-triggered $LXA_4$. (A) 5-LO (−/−) and (+/+), and (B) hBLTR transgenic and wt mice were subject to hind limb ischemia-reperfusion. The left lungs were collected. MPO activities were determined, and data are expressed as (A) fold increase in lung PMN infiltrates compared to control animals (ischemia alone) from two separate experiments and (B) total PMN infiltration into lungs after ischemia-reperfusion. Total PMN numbers obtained from hBLTR transgenic and wt mice were significantly different (*p=0.02, n=3). (C) Balb/c mice were subject to ischemia-reperfusion (~0.8 ng, filled bar) or ischemia alone (~0.5 ng, hatched bar). After removal of hind limb tourniquet, left lungs were collected with or without reperfusion. $LXA_4$ present within each lung tissue was quantitated by ELISA (Neogen, Lexington, Ky.) or LC/MS/MS. (D) hBLTR transgenic mice were injected with vehicle (hatched bar) or the ATL analog (10 µg, inset: ATL analog template $R_2$=para-fluoro-phenoxy) (filled bar). Leukocyte MPO values were obtained from left lung of each mouse after ischemia-reperfusion and expressed as percent inhibition of lung PMN infiltration. Values from mice that received ATL analog vs. vehicle alone (~12×10$^5$ PMN) were significantly different (*p=0.04, n=3).
Figure 2B:
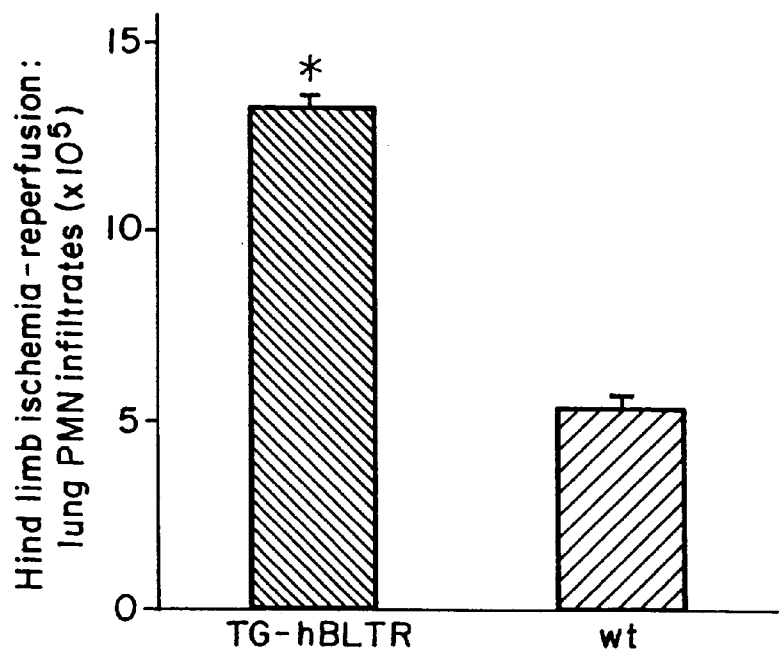
Figure 3A:
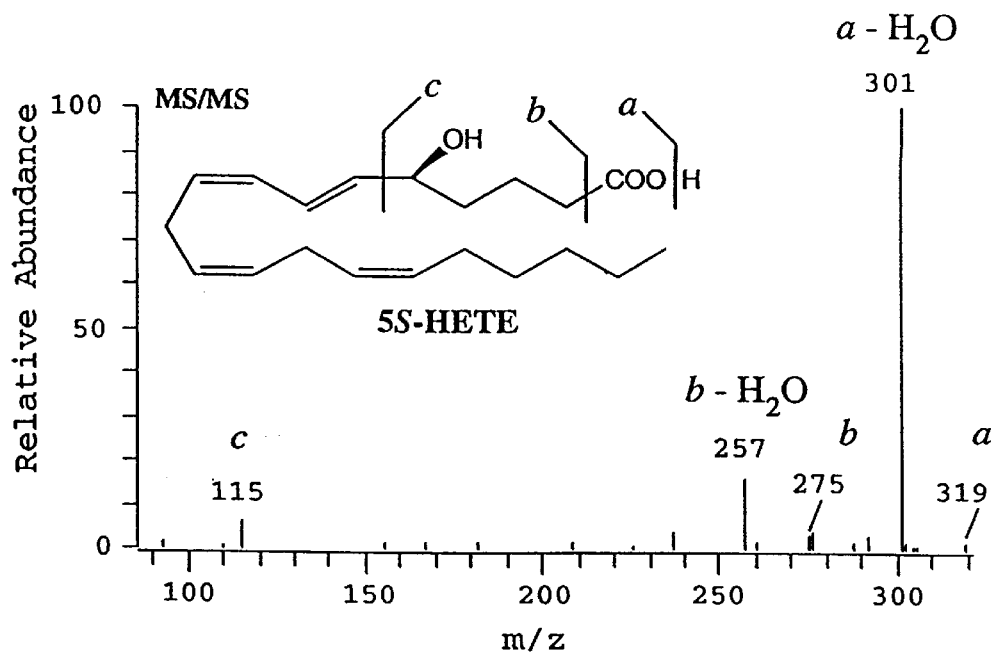
FIG. 3 (A–B) depicts a positive feedback loop in hBLTR transgenic mice: 5-LO transcripts and 5S-HETE are upregulated in peritonitis. (A) MS/MS spectrum of 5S-HETE. Peritoneal leukocytes from casein-induced peritonitis were collected and analyzed by LC/MS/MS. SIM chromatograms at m/z 319 as well as MS/MS spectra of 5S-HETE were acquired with a Finnigan LCQ LC/MS/MS. 5S -HETE was identified by its diagnostic MS/MS product ions at m/z =319 (a), 301 (a-$H_2O$), 275 (b), 257 (b-$H_2O$) and 115 (c). (B) Levels of 5S-HETE, 15S-HETE and 12S-HETE in wt (hatched bar) and hBLTR transgenic mice (filled bar) were quantitated by LC/MS/MS and expressed in pg/5×10$^5$ peritoneal exudate leukocytes (*p<0.01, n=3). Total RNA from exudate leukocytes of wt and hBLTR transgenic mice was isolated and analyzed by RT-PCR using mouse 5-LO specific primers that gave the expected band at ~0.3 kb indicated by an arrow (inset).

Ischemia-reperfusion is an event with major clinical importance. To evaluate the contribution of both BLTR and LT formation in reperfusion injury, a hind limb tourniquet model of second organ injury with both 5-LO deficient and hBLTR transgenic mice (FIG. 2A and B) was utilized (Goldman, G., Welbourn, R., Klausner, J. M., Kobzik, L., Valeri, C. R. et al. 1992. Mast cells and leukotrienes mediate neutrophil sequestration and lung edema after remote ischemia in rodents. *Surgery* 112: 578–586). In humans, surgical based clamping procedures are well known to lead to aberrant PMN activation, giving rise to second organ injury that contributes to longer hospitalization (Gelman, S. 1995. The pathophysiology of aortic cross-clamping and unclamping. *Anesthesiology* 82: 1026–1060). 5-LO (+/+) and (−/−) mice gave ~10 fold and ~5 fold increases in leukocyte accumulation in lungs, respectively, compared to sham operated mice (FIG. 2A), indicating that 5-LO derived products (e.g. $LTB_4$, see inset in FIG. 3) are major mediators of PMN recruitment into lungs following hind limb ischemia-reperfusion. Pharmacological evidence implicated $LTB_4$ as a component in ischemia-reperfusion-induced second organ injury in mice and rats (Goldman, G., Welbourn, R., Klausner, J. M., Kobzik, L., Valeri, C. R. et al. 1992. Mast cells and leukotrienes mediate neutrophil sequestration and lung edema after remote ischemia in rodents. *Surgery* 112: 578–586; Seekamp, A. and Ward, P. A. 1993. Ischemia-reperfusion injury. Agents Actions (Suppl.) 41: 137–152)). Results with PMN recruitment in 5-LO (−/−) mice also illustrated the contribution of other mediators, such as C5a, IL-8 and PAF, since PMN recruitment occurs in the absence of endogenous $LTB_4$ formation (FIG. 2A) (Gronert, K., Colgan, S. P. and Serhan C. N. 1998. Characterization of human neutrophil and endothelial cell ligand-operated extracellular acidification rate by microphysiometry: impace of reoxygenation. *J. Phar. Exp. Ther.* 285: 252–261). The hBLTR transgenic mice also showed dramatic increases in PMN infiltration into lungs following reperfusion compared to wt mice (FIG. 2B). Results from these genetically manipulated mice, namely 5-LO deficient and hBLTR transgenic, when taken together demonstrate that both the enhanced appearance of BLTR and LT formation are important events in ischemia-reperfusion induced second organ injury and therefore are potential therapeutic targets for further consideration in perioperative treatment.

Figure 2C:
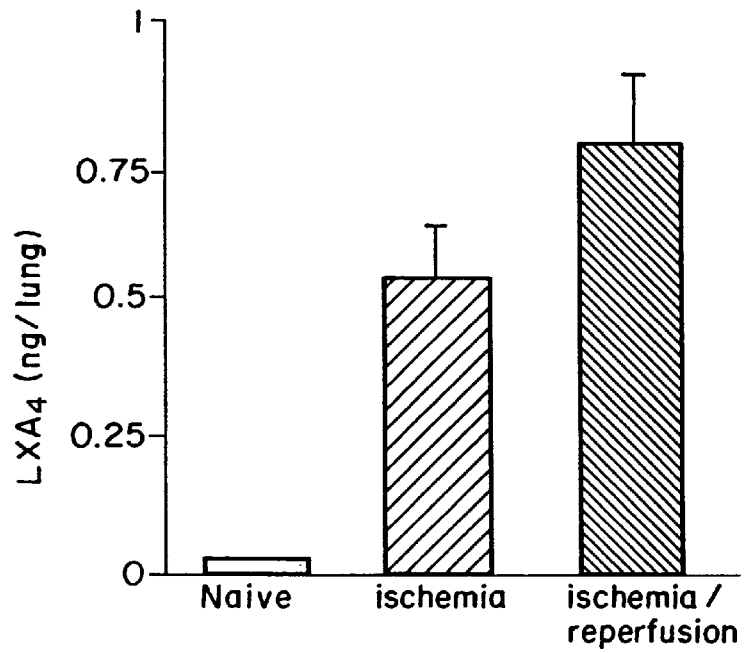
Figure 2D:
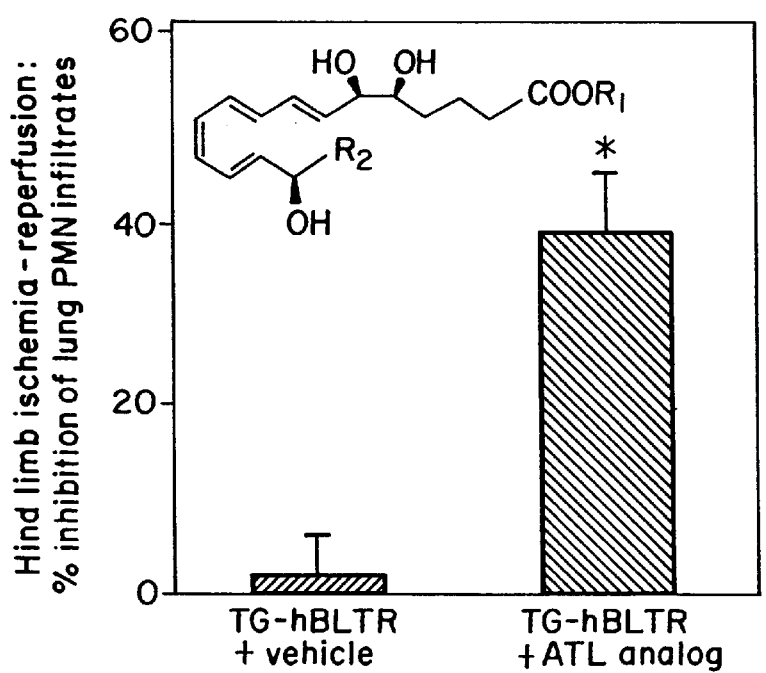

In view of the ability of $LXA_4$ to modulate PMN-directed responses, it was of interest to determine whether $LXA_4$ is generated during ischemia-reperfusion and whether it has an impact in the transgenic amplified BLTR signaling (Serhan, C. N. 1997. Lipoxins and novel aspirin-triggered 15-epi-lipoxins (ATL) *Prostaglandins* 53: 107–137). Hind limb ischemic mice showed increased amounts of endogenous $LXA_4$ in lungs, and tourniquet release (reperfusion) further increased these levels (FIG. 2C). Therefore, an aspirin-triggered $LXA_4$ (ATL) analog (see FIG. 2D inset for 15-epi-$LXA_4$ analog template structure) was administered via intravenous injection in hBLTR transgenic mice prior to hind limb ischemia-reperfusion. The administration of ATL significantly diminished PMN infiltration into lungs when compared to hBLTR transgenic mice injected with vehicle alone (FIG. 2D). Thus, $LXA_4$ formation within ischemic tissue and its elevation by reperfusion might represent an endogenous compensatory or protective role to limit PMN trafficking and PMN mediated damage. This is supported by results with intravascular injection of the ALXR agonist (e.g., ATL stable analogs that are longer-acting than the endogenous $LXA_4$, cf.) prior to ischemia-reperfusion, which attenuates BLTR- driven PMN infiltration (Serhan, C. N. 1997. Lipoxins and novel aspirin-triggered 15-epi-lipoxins (ATL) *Prostaglandins* 53: 107–137; Takano, T., Clish, C. B., Gronert, K., Petasis, N. A. and Serhan C. N. 1997. Neutrophil-mediated changes in vascular permeability are inhibited by topical application of aspirin-triggered 15-epi-lipoxin $A_4$ and novel lipoxin $B_4$ stable analogues. *J. Clin. Invest.* 101: 819–826). In addition, since ATL inhibited PMN infiltration, at ≈ the reciprocal level (40–60% change) observed in either the 5-LO (−/−) or in BLTR transgenic mice (FIG. 2A, B and D), their reciprocity emphasizes the importance of the $LXA_4$-$LTB_4$ regulatory system in these genetically defined mice.

Figure 3B:
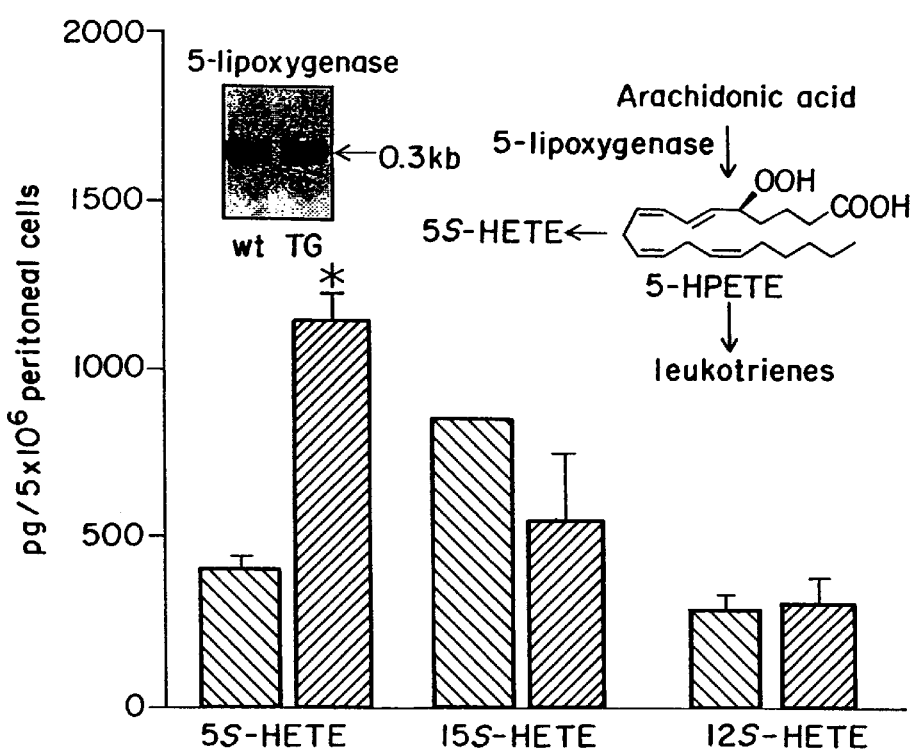

Of interest, with BLTR transgenic mice it was found, using systematic liquid chromatography-tandem mass spectrometry (LC/MS/MS) based analysis, that 5S-HETE (FIG. 3A) (a product of 5-LO, see inset of FIG. 3B) generation was selectively and dramatically elevated in peritoneal inflammatory exudates compared to wt (FIG. 3B). In contrast, significant differences were not observed in the amount of other mono-HETEs from the major lipoxygenase pathways including 15S-HETE, 12S-HETE (FIG. 3B) or $LTB_4$. It is noteworthy that 5S-HETE is also a PMN chemoattractant, albeit less potent than $LTB_4$ (Capodici, C., Pillinger, M. H., Han, G., Philips, M. R. and Weissmann, G. 1998. Integrin-dependent homotypic adhesion of neutrophils. Arachidonic acid activates Raf-1/Mek/Erk via a 5-lipoxygenase- dependent pathway. *J. Clin. Invest.* 102: 165–174). Expression of 5-LO transcript in peritoneal leukocytes was ~3.5 fold higher in hBLTR transgenic mice (FIG. 3B inset). The observed increase in 5S-HETE rather than $LTB_4$ in BLTR transgenic mice may reflect enhanced $LTB_4$ utilization and clearance (i.e., further metabolism) in this model. No apparent increases in cyclooxygenase-2 message levels were noted. Also, striking elevations in cyclooxygenase products (e.g., prostaglandin $E_2$) were not observed in LC/MS/MS analyses. Thus, the overexpression of BLTR specifically enhances a pro-inflammatory network by acting at the level of 5-LO gene transcription that is evident in vivo (FIG. 3B), suggesting that this positive feedback within the 5-LO pathway could be operative in a wide range of disease states.

The present findings provide the first demonstration that overexpression of BLTR profoundly amplifies PMN recruitment, function and 5-LO signaling in murine models of acute skin inflammation, peritonitis and reperfusion-initiated second organ injury. In addition, these independent lines of investigation, when taken together, provide the first direct evidence for an in vivo role of BLTR expression in regulating PMN activation and up-regulation of the 5-LO pathway. Together, they emphasize the impact of receptor expression as important regulatory steps in host responses as well as ischemia-reperfusion and are consistent with the regulation of ALXR (Gronert, K., Gewirtz, A., Madara, J. L. and Serhan, C. N. 1998. Identification of a human enterocyte lipoxin $A_4$ receptor that is regulated by interleukin (IL)-13 and interferon γ and inhbits tumor necrosis factor α-induced IL-8 release. *J. Exp. Med.* 187: 1285–1294) and BLTR (Huang, W—W., Garcia-Zepeda, E. A., Sauty, A., Ottegen, H. C., Rothenberg, M. E. et al. 1998. Molecular and biological characterization of the murine leukotriene $B_4$ receptor expressed on eosinophils. *J. Exp. Med.* 188: 1063–1074) expression by cytokines that are linked to the control of human immune functions. Moreover, these results open new avenues for the utility of counter-regulatory signals, namely ALXR agonists and stable aspirin-triggered LX, to selectively regulate inflammatory diseases and reperfusion-associated injury events that are characterized and exacerbated by excessive PMN infiltration and activation.

References

1. Weissmann, G., Smolen, J. E., and Korchak, H. M. 1980. Release of inflammatory mediators from stimulated neutrophils. *N. Engl. J. Med.* 303: 2734.

2. Sammuelsson, B. 1983. Leukotrienes: Mediators of inflammation and immediate hypersensitivity. *Science* 220: 568–575.

3. Owman, C. 1998. The leukotriene $B_4$ receptor functions as a novel type of coreceptor mediating entry of primary HIV-1 isolates into CD4-positive cells. *Proc. Natl. Acad. Sci. USA* 95: 9530–9534.

4. Marcus, A. J. 1995. Aspirin as prophylaxis against colorectal cancer. *N. Eng. J. Med.* 333:656–658.

5. Serhan, C. N. 1997. Lipoxins and novel aspirin-triggered 15-epi-lipoxins (ATL) *Prostaglandins* 53: 107–137.

6. Chiang, N., Takano, T., Clish, C. B., Petasis, N. A. and Serhan C. N. 1998. Aspirin-triggered 15-epi-Lipoxin $A_4$ (ATL) generation by human leukocytes and murine peritonitis exudates: development of a specific 15-epi-$LXA_4$ ELISA. *J. Phar. Exp. Ther.* 287: 77914 790.

7. Takano, T., Clish, C. B., Gronert, K., Petasis, N. A. and Serhan, C. N. 1997. Neutrophil-mediated changes in vascular permeability are inhibited by topical application of aspirin-triggered 15-epi-lipoxin $A_4$ and novel lipoxin $B_4$ stable analogues. *J. Clin. Invest.* 101: 81914 826.

8. Yokomizo, T., Izumi, T., Chang, K., Takuwa, Y. and Shimizu, T. 1997. A G-protein-coupled receptor for leucotriene $B_4$ that mediates chemotaxis. *Nature* 387: 620–624.

9. Huang, W. -W., Garcia-Zepeda, E. A., Sauty, A., Oettgen, H. C., Rothenberg, M. E. et al. 1998. Molecular and biological characterization of the murine leukotriene $B_4$ receptor expressed on eosinophil. *J. Exp. Med.* 188: 1063–1074.

10. Toh, H., Ichikawa, A. and Narumiya, S. 1995. Molecular evolution of receptors for eicosanoids. *FEBS Letters* 361: 17–21.

11. Funk, C. D. 1999. In "Molecular and Cellular Basis of Inflammation" (eds. C. N. Serhan and P. A. Ward) Lipid-mediator-deficient mice in models of inflammation, pp. 109–125. Humana Press, Totowa, N.J.

12. Fiore, S., Romano, M., Reardon, E. M. and Serhan, C. N. 1993. Induction of functional lipoxin $A_4$ receptors in HL-60 cells. *Blood* 81: 3395–3403.

13. Ng, C. F., Sun, F. F., Taylor, B. M., Wolin, M. S. and Wong, P. Y. 1991. Functional properties of guinea pig eosinophil leukotriene $B_4$ receptors. *J. Immunol.* 147: 3096–3103

14. Gronert, K., Colgan, S. P. and Serhan, C. N. 1998. Characterization of human neutrophil and endothelial cell ligand-operated extracellular acidification rate by microphysiometry: impact of reoxygenation. *J. Phar. Exp. Ther.* 285: 252–261.

15. Goldman, G., Welbourn, R., Klausner, J. M., Kobzik, L., Valeri, C. R. et al. 1992. Mast cells and leukotrienes mediate neutrophil sequestration and lung edema after remote ischemic in rodents. *Surgery* 112: 578–586.

16. Chen, X. -S., Sheller, J. R., Johnson, E. N. and Funk, C. D. 1994. Role of leukotrienes revealed by targeted disruption of the 5-lipoxygenase gene. *Nature* 372: 179–182.

17. Dziennis, S., Van Etten, R. A., Pahl, H. L., Morris, D. L., Rothstein, T. L. et al. 1995. The CD11b promoter directs high-level expression of reporter genes in macrophage in transgenic mice. *Blood* 85: 319–329.

18. Gelman, S. 1995. The pathophysiology of aortic cross-clamping and unclasping. *Anesthesiology* 82: 1026–1060.

19. Seekamp, A. and Ward, P. A. 1993. Ischemia-reperfusion injury. *Agents Actions (Suppl.)* 41: 137–152.

20. Capodici, C., Pillinger, M. H., Han, G., Phillips, M. R. and Weissmann, G. 1998. Integrin-dependent homotypic adhesion of neutrophils. Arachidonic acid activates Raf-1/Mek/Erk via a 5-lipoxygenase-dependent pathway. *J. Clin. Invest.* 102: 165–175.

21. Gronert, K., Gewirtz, A., Madara, J. L. and Serhan, C. N. 1998. Identification of a human enterocyte lipoxin $A_4$ receptor that is regulated by interleukin (IL)-13 and interferon γ and inhibits tumor necrosis factor α-induced IL-8-release. *J. Exp. Med.* 187: 1285–1294.

One of ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. A transgenic mouse that produces in its leukocytes a recombinant human leukotriene $B_4$ receptor (hBLTR), wherein said transgenic mouse has stably integrated into its genome an exogenous expression vector that comprises a nucleotide sequence comprising a CD11b promoter in operable linkage with a nucleotide sequence encoding said hBLTR, and wherein expression of said hBLTR results in an increased recruitment of polymorphonuclear neutrophils (PMN) in response to acute skin inflammation, peritonitis, or ischemia reperfusion injury, in said mouse.

2. The transgenic mouse according to claim 1, wherein said transgenic mouse is female.

3. A method for producing recombinant hBLTR comprising:
  A) providing the transgenic mouse of claim 1; and
  B) allowing said hBLTR to be produced and secreted in the leukocytes of said transgenic mouse.

4. The method according to claim 3, wherein said transgenic mouse is female.

5. A method for producing the transgenic mouse of claim 1 comprising:
  a) providing an exogenous expression vector that comprises a nucleotide sequence comprising a CD11b promoter in operable linkage with a nucleotide sequence encoding said hBLTR;
  b) introducing the expression vector of step (a) into a fertilized mouse oocyte;
  c) allowing said fertilized mouse oocyte to develop to term; and
  d) identifying a transgenic mouse whose genome comprises the hBLTR nucleotide sequence, wherein expression of said hBLTR results in an increased recruitment of polymorphonuclear neutrophils (PMN) in response to acute skin inflammation, peritonitis, or ischemia reperfusion injury, in said mouse.

6. The method according to claim 5, wherein said transgenic mouse is female.

7. A method for screening compounds that inhibit the recruitment of polymorphonuclear neutrophils (PMN) in a transgenic mouse that produces in its leukocytes recombinant hBLTR, comprising:
  a) providing the transgenic mouse of claim 1;
  b) allowing said hBLTR to be produced and secreted in said leukocytes of said transgenic mouse;

c) physiologically stressing said transgenic mouse, thereby causing increased neutrophil recruitment to the area of physiological stress;

d) administering a compound to interact with said neutrophil recruitment in response to said physiological stress; and e) determining whether said compound reduces neutrophil recruitment in response to said physiological stress.

8. The method according to claim 2, wherein said transgenic mouse is female.

9. The method for screening compounds that prevent the recruitment of polymorphonuclear neutrophils (PMN) in a transgenic mouse that produces in its leukocytes recombinant hBLTR, comprising:

a) providing the transgenic mouse of claim 1;

b) allowing said hBLTR to be produced and secreted in said leukocytes of said transgenic mouse;

c) administering a compound to prevent said neutrophil recruitment in response to physiological stress;

d) physiologically stressing said transgenic mouse; and e) determining whether said compound prevents neutrophil recruitment in response to said physiological stress.

* * * * *